(12) United States Patent
Asleson et al.

(10) Patent No.: US 11,559,669 B2
(45) Date of Patent: Jan. 24, 2023

(54) CANNULA DELIVERY CATHETER AND PROCEDURE METHOD

(71) Applicant: Medtronic, Inc., Minneapolis, MN (US)

(72) Inventors: Andrea J. Asleson, Maple Grove, MN (US); Michael P. Campbell, Blaine, MN (US); Teresa Whitman, Dayton, MN (US); Keith D. Anderson, Minneapolis, MN (US); Bridget A. Portway, White Bear Township, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 146 days.

(21) Appl. No.: 16/375,486

(22) Filed: Apr. 4, 2019

(65) Prior Publication Data
US 2020/0316351 A1    Oct. 8, 2020

(51) Int. Cl.
| | |
|---|---|
| *A61M 25/10* | (2013.01) |
| *A61M 25/00* | (2006.01) |
| *A61M 25/01* | (2006.01) |

(52) U.S. Cl.
CPC .... *A61M 25/1025* (2013.01); *A61M 25/0074* (2013.01); *A61M 25/005* (2013.01);
(Continued)

(58) Field of Classification Search
CPC .. A61M 2025/0004; A61M 2025/0175; A61M 2025/1061; A61M 2025/1093;
(Continued)

(56) References Cited

U.S. PATENT DOCUMENTS

| | | | | |
|---|---|---|---|---|
| 5,219,329 A | * | 6/1993 | Fischell | A61B 17/22031 604/249 |
| 5,413,561 A | * | 5/1995 | Fischell | A61M 39/0606 604/167.01 |

(Continued)

FOREIGN PATENT DOCUMENTS

| | | |
|---|---|---|
| WO | 0187174 A1 | 11/2001 |
| WO | 2006029370 A2 | 3/2006 |
| WO | 2012109557 A2 | 8/2012 |

OTHER PUBLICATIONS

Mohamad Alkhouli, MD, et al., Transseptal Techniques for Emerging Structural Heart Interventions, JACC: Cardiovascular Interventions, vol. 9, No. 24, 2016.
(Continued)

*Primary Examiner* — Shefali D Patel
(74) *Attorney, Agent, or Firm* — Shumaker & Sieffert, P.A.

(57) ABSTRACT

The medical device may comprise an elongate body having a proximal portion, a distal portion, and defining a lumen therethrough. Also, the medical device may include an expandable element coupled to the distal portion of the elongate body and in fluid communication with the lumen. The expandable element may define a first end and a second end, the second end being proximal to the first end. The medical device may further include a cannula surrounding at least a portion of the elongate body and the cannula may define a proximal end and a distal end. The distal end of the cannula may be disposed proximal and adjacent to the second end of the expandable element. An outer dimeter diameter of the cannula may be substantially equal to or lesser than an outer diameter of the expandable element when inflated. The medical device may be maneuvered through a patient's body.

19 Claims, 5 Drawing Sheets

(52) U.S. Cl.
CPC ..... *A61M 25/0054* (2013.01); *A61M 25/0068* (2013.01); *A61M 25/0082* (2013.01); *A61M 25/0136* (2013.01); *A61M 2025/1093* (2013.01); *A61M 2210/125* (2013.01)

(58) Field of Classification Search
CPC .......... A61M 25/0068; A61M 25/0074; A61M 25/10; A61M 25/1006; A61M 25/1025; A61M 2210/125; A61M 39/06; A61M 39/22; A61M 2039/062; A61M 25/005; A61M 25/0054; A61M 25/0082; A61B 2017/00247
See application file for complete search history.

(56) References Cited

U.S. PATENT DOCUMENTS

| | | | |
|---|---|---|---|
| 2002/0169377 A1* | 11/2002 | Khairkhahan | A61B 17/32075 600/433 |
| 2006/0135962 A1* | 6/2006 | Kick | A61M 25/09 606/108 |
| 2007/0179527 A1 | 8/2007 | Eskuri et al. | |
| 2007/0225760 A1 | 9/2007 | Moszner et al. | |
| 2009/0048668 A1 | 2/2009 | Wilson | |
| 2009/0326572 A1 | 12/2009 | Peh et al. | |
| 2010/0022948 A1* | 1/2010 | Wilson | A61M 25/0147 604/95.04 |
| 2011/0184400 A1 | 7/2011 | Pageard | |
| 2014/0296908 A1 | 10/2014 | Ottma et al. | |
| 2014/0309675 A1* | 10/2014 | Maisano | A61B 17/3478 606/170 |
| 2015/0066077 A1 | 3/2015 | Akpinar | |
| 2016/0263302 A1 | 9/2016 | Klepetko | |
| 2020/0316275 A1 | 10/2020 | Asleson et al. | |

OTHER PUBLICATIONS

International Search Report and Written Opinion dated May 15, 2020, for corresponding International Application No. PCT/US2020/019487; International Filing Date: Feb. 24, 2020 consisting of 11 pages.

Sree Karanam, MD, et al., Balloon Dilatation of the Atrial Septum to Facilitate Trans-septal Access to the Left Atrium, The Journal of Innovations in Cardiac Rhythm Management. Manuscript, final version accepted Mar. 7, 2011.

SickKidsStaff, Balloon atrial septostomy, https://www.aboutkidshealth. ca/Article?contentid=1668&language=English, last updated Jul. 11, 2016.

International Preliminary Report on Patentability from International Application No. PCT/US2020/019487, dated Sep. 28, 2021, 7 pp.

* cited by examiner

CANNULA DELIVERY CATHETER AND PROCEDURE METHOD

CROSS-REFERENCE TO RELATED APPLICATION n/a

STATEMENT REGARDING FEDERALLY SPONSORED RESEARCH OR DEVELOPMENT n/a

FIELD

The present technology is generally related to a catheter and cannula and a method for using the catheter and cannula within a patient's heart.

BACKGROUND

Access to the left atrium of the heart is frequently required in cardiac treatment procedures. In order to access the left atrium of the heart, a medical device delivery system may be used to enter into the vasculature of a patient including the right subclavian vein, the superior vena cava, the right atrium, and the atrial septum and then a cannula, which may be large or small depending upon what it is going to be used for, may be fixated into the septum of the heart. The medical device delivery system may be composed of a variety of different tools that are introduced into a patient's vasculature. However many issues may arise during this process as the medical device delivery system and all of its separate components have to safely and efficiently move through portions of the body.

The initial introduction of the medical device delivery system into the vasculature can be difficult based upon the size of the medical device delivery system in comparison to the vasculature. Additionally, after the initial introduction of the medical device delivery system, a cannula, as well as other equipment may need to be separately introduced into the vasculature. The medical device delivery system, the cannula, and other equipment often experience issues moving through the vasculature and can get stuck, cause plaque to come off the walls of the vasculature, puncture holes in the vasculature as well as cause other issues depending upon the dimensions and rigidity of the medical device delivery system, the catheter, and the other equipment. Damage to the vascular system or other parts of the body can cause significant medical issues and problems that may not be able to be repaired and/or cause long-term medical problems for the patient.

When the medical device delivery system moves through the septum of the heart, it may make a hole in the septum that is larger than the cannula that is going to be fixated in the hole and can create difficulties when trying to fixate the cannula into the septum. Additionally, the medical device delivery system may not have enough support and rigidity to cross the septum into the left atrium of the heart and then the cannula cannot be placed in the septum.

The use of the medical device delivery system often requires the use of various delivery tools. It can take a significant amount of time to clean and prepare all the tools before they are introduced into a patient's vasculature. The use of the different tools can make it difficult to effectively and efficiently perform a medical procedure. There is no simple and safe way to move a medical device delivery system as well as a cannula through the body and heart and into the atrial septum without causing injury to tissue and possibly causing significant injuries.

SUMMARY

In accordance with the present invention, various devices, components, and methods associated with a cannula delivery catheter are set forth. The present invention advantageously provides a medical device. The medical device may comprise an elongate body having a proximal portion, a distal portion, and defining a lumen therethrough; an expandable element being coupled to the distal portion of the elongate body and in fluid communication with the lumen, the expandable element defining a first end and a second end, the second end being proximal to the first end; a cannula surrounding at least a portion of the elongate body, the cannula defining a proximal end and a distal end, the distal end of the cannula being disposed proximal and adjacent to the second end of the expandable element; and an outer dimeter of the cannula being substantially equal to or lesser than an outer diameter of the expandable element when inflated.

In one aspect of the embodiment, the expandable element is a balloon.

In another aspect of this embodiment, the balloon is constructed from at least one from the group consisting of polyethylene terephthalate, nylon, polyurethane, and latex.

In another aspect of this embodiment, the cannula is coaxial with the elongate body.

In another aspect of this embodiment, the medical device further comprises a tip with an aperture in fluid communication with the lumen, the tip being disposed on the distal portion of the elongate body.

In another aspect of this embodiment, the tip has a proximal portion, a distal portion, and a longitudinal axis extending therethrough, the tip tapering in diameter from the proximal portion to the distal portion along the longitudinal axis and configured to enlarge and orifice created by a puncturing device.

In another aspect of this embodiment, the distal end of the cannula is substantially co-terminus with the second end of the expandable element.

In another aspect of this embodiment, the elongate body is constructed from a block copolymer.

In another aspect of this embodiment, the outer diameter of the cannula and the outer diameter of the expandable element are at least 8.5 millimeters.

In another aspect of this embodiment, the outer diameter of the cannula and the outer diameter of the expandable element are less than 8.5 millimeters.

In another aspect of this embodiment, the cannula and the elongate body are coupled together.

In another aspect of this embodiment, the elongate body further includes a longitudinal axis extending from the proximal portion to the distal portion, the cannula being slidable with respect to the elongate body along the longitudinal axis.

In another aspect of this embodiment, the lumen has a diameter of between 0.010 inches and 0.060 inches.

In another embodiment, a medical device comprising: an elongate body having a proximal portion and a distal portion, the elongate body defining a lumen therethrough; at least one expandable element surrounding the distal portion of the elongate body configured to expand to a first diameter and defining a first end and a second end, the first end being opposite the second end; a cannula disposed around the elongate body and substantially co-terminus with the second end of the expandable element, the cannula having a second diameter that is substantially the same as the first diameter; and the distal portion of the elongate body further including a tip with a proximal portion, a distal portion, a longitudinal axis extending therethrough, and an aperture which is in fluid communication with the lumen, the tip tapering in diameter from the proximal portion to the distal portion along the longitudinal axis and being configured to enlarge an orifice created by a puncturing device.

In another aspect of this embodiment, the at least one expandable element is at least one balloon.

In another aspect of this embodiment, the at least one balloon is constructed from at least one of the group consisting of polyethylene terephthalate, nylon, polyurethane, and latex.

In another aspect of this embodiment, the first diameter and the second diameter are at least 8.5 millimeters.

In another aspect of this embodiment, the at least one expandable element further includes a longitudinal axis extending from the first end to the second end and the length of the at least one expandable element along the longitudinal axis is between 1 cm and 6 cm.

In another aspect of this embodiment, the elongate body is constructed from a block copolymer.

In another embodiment, the method for delivering a cannula comprises: positioning a medical device proximate the fossa ovalis of a patient's heart, the medical device including: an elongate body having a proximal portion, a distal portion, and defining a lumen therethrough; an expandable element being coupled to the distal portion of the elongate body and in fluid communication with the lumen, the expandable element defining a first end and a second end, the second end being proximal to the first end; a cannula surrounding at least a portion of the elongate body, the cannula defining a proximal end and a distal end, the distal end of the cannula being disposed proximal and adjacent to the second end of the expandable element; an outer dimeter of the cannula being substantially equal to or lesser than an outer diameter of the expandable element when inflated; and the distal portion of the elongate body further including a tip. Advancing a puncturing device through the lumen of the medical device; puncturing the fossa ovalis with the puncturing device to create an orifice; withdrawing the puncturing device through the lumen; inserting the tip into the orifice; advancing the medical device through the orifice until at least a portion of the expandable element is in contact with the fossa ovalis surrounding the orifice; expanding the expandable element to a first diameter, the first diameter being substantially the same diameter as the diameter of the cannula; continuing to advance the medical device until the cannula is in contact with the expanded orifice; deflating the expandable element; and withdrawing the expandable element leaving the cannula in contact with the expanded orifice.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Before describing in detail exemplary embodiments, it is noted that the embodiments reside primarily in combinations of device and system components related to a medical device.

Accordingly, the device and system components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Figure 1:
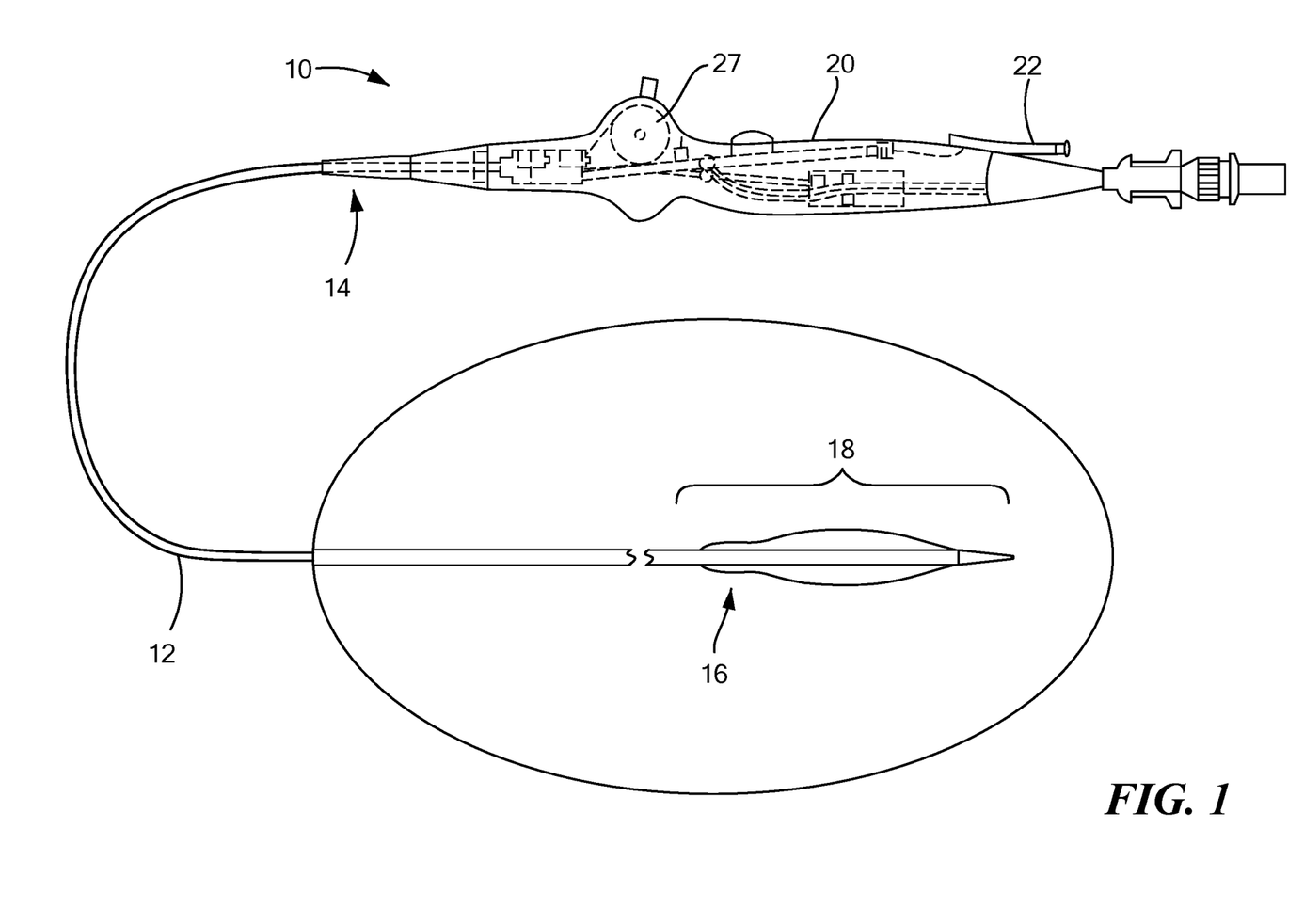
FIG. 1 is a perspective view of a medical device constructed in accordance with an embodiment of the present invention.

Referring now to the drawings in which like reference designators refer to like elements, there is shown in FIG. 1 an exemplary medical device constructed in accordance with the principles of the present application and designated generally as 10. The medical device 10, according to one embodiment of the disclosure, may be configured to be maneuvered through a patient's vascular system, or another portion of a patient's body. As a non-limiting example, the medical device 10 may be navigated from the right subclavian vein, through the superior vena cava, and into the right atrium, and the medical device 10 may be used to puncture the atrial septum, such as through the area of septal tissue known as the fossa ovalis, to gain access into the left atrium.

The medical device 10 may also be maneuvered through other areas of the body as well.

With reference to FIG. 1, the medical device 10 may generally define an elongated and flexible catheter body 12 with a proximal end 14 and a distal end 16 having a distal portion 18 as well as a handle 20 at the proximal end 14 of the catheter body 12. The catheter of the present invention may be sized and dimensioned for intraluminal and transseptal access to a patient's heart. The catheter body 12 may be formed and dimensioned to provide sufficient column and torsional strength to support standard interventional procedures such as those which access the vasculature from a femoral vein or artery and further access the patient's heart. The catheter shaft may include reinforcement elements or otherwise be constructed to provide desired degrees of stiffness, flexibility, and torque transmission along the length of the body and at selected locations along its length. The catheter body 12 may have portions or components of differing size, thickness or flexibility, and may include wires, braiding, changes in wall thickness, additional wall layers or catheter body 12 components, sleeves, or other components reinforcing or otherwise supplementing an outer wall or thickness along its length. Some portions that may experience significant loading or torque during a particular procedure may also include reinforcement. For example, the catheter body 12 may be a braided prebax shaft with different durometer segments to create the desired curve within the catheter body 12 depending upon where and how the medical device 10 is going to be maneuvered in the body. The braiding of the prebax shaft may provide resistance and torque to the catheter body 12.

FIG. 1 depicts a medical device 10 with a handle 20. The handle 20 may include one port 22 or more than one port 22. As a non-limiting example, the one port 22 may be configured to receive a device which may include a puncturing device 24 and/or a guidewire 26. In one example, the catheter body 12 may be configured to receive the puncturing device 24 and/or a guidewire 26 having a diameter of approximately 0.035 inches such that the catheter body 12 has an inner diameter of approximately 0.040 inches and an outer diameter of the catheter body 12 may be between approximately 0.100 inches and 0.130 inches to accommodate the diameter of the guidewire 26 and/or the puncturing device 24. Additionally, a different port 22 or the same port 22 may be configured to receive an inflation and deflation lumen as well as other devices that may be used with the medical device 10. The handle 20 may also have additional ports 22 and is not limited to one or two ports 22 and the port 22 may be configured to receive a variety of different devices depending upon how and where the medical device 10 is being used.

The handle 20 may further include an actuator 27 in communication with a deflection element (not shown) configured to move at least a portion of the catheter body 12 in any direction. As a non-limiting example, the deflection element may be a wire configured to fit within the catheter body 12. The wire within the catheter body 12 may extend to the distal portion 18 or anywhere within the catheter body 12. The actuator 27 may have a moveable component configured to move the deflection element in a particular direction. When the moveable component on the actuator 27 is moved in a particular direction, a portion of the catheter body 12, including the distal portion 18, can move to the left, right, and/or up or down. For example, the movable component may be a bar which is attached to the actuator 27 that can be moved up and down, the upwards movement of the bar moves the deflection element upwards and the downwards movement of the bar moves the deflection element downwards. If the movable component includes a button, depressing the button moves the deflection element to the left and lifting the button upwards moves the deflection element to the right. Other movable components may be used to move a portion of the catheter body 12 in any direction.

Figure 2:
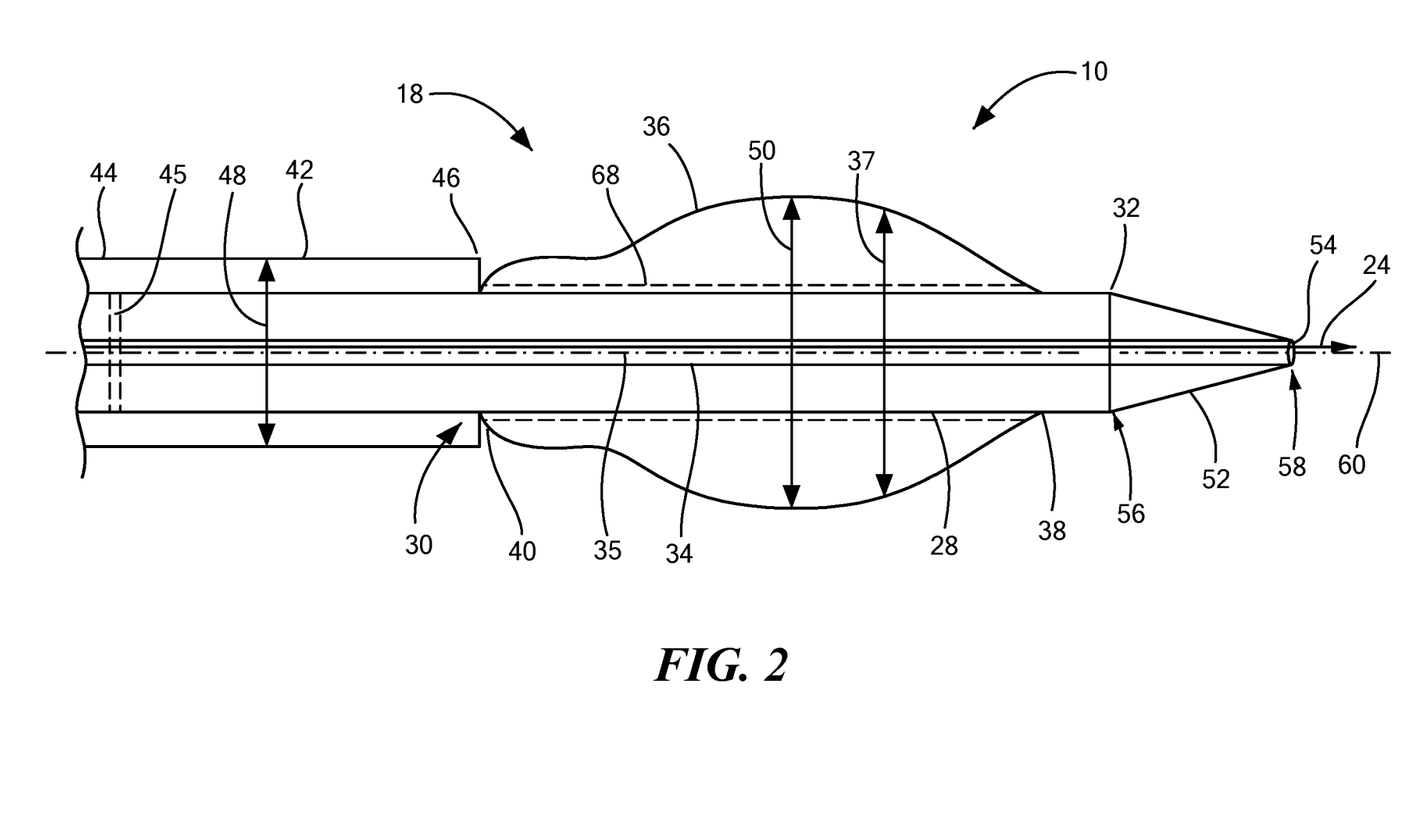
FIG. 2 is a perspective view of a distal portion from the medical device in FIG. 1.

One configuration of the distal portion 18 of the medical device 10 is shown in FIG. 2. The distal portion 18 may include an elongate body 28 with a proximal portion 30 of the elongate body 28, a distal portion 32 of the elongate body 28 and defining a lumen 34 therethrough. The elongate body 28 may further include a longitudinal axis 35 which extends from the proximal portion 30 to the distal portion 32 of the elongate body 28. The elongate body 28 may be constructed from a block co-polymer or another type of co-polymer. Alternatively, the elongate body 28 may be constructed from a metal or non-metal material that is safe to be used within the body. The lumen 34 may be sized to receive different devices and/or infusions. In one example, the lumen 34 may have a diameter of between 0.010 inches and 0.060 inches. In alternative embodiments, the diameter of the lumen may be smaller than 0.010 inches and it may also be larger than 0.060 inches to accommodate different size devices as well as different sizes and shapes of different anatomical structures. An expandable element 36 may be coupled to the distal portion 32 of the elongate body 28 and be in fluid communication with the lumen 34. Where the expandable element 36 is in fluid communication with the lumen 34, a gas or a liquid may be used to inflate or deflate the expandable element 36 to different sizes and shapes. The sizes and shapes of the expandable element 36 may be changed as the expandable element 36 is maneuvered through different portions of the body including different anatomical structures.

The expandable element 36 may have a first end 38 and a second end 40 and the second end 40 may be proximal to the first end 38 and the first end 38 may be opposite the second end 40. The expandable element 36 may refer to one expandable element 36 or more than one expandable element 36. For example, in one configuration, there may be one expandable element 36 while in another configuration there may be more than one expandable element 36. The expandable element may be inflatable to at least one diameter 37. For example, the expandable element 36 may be inflated such that the expandable element 36 has one continuous diameter. Alternatively, the expandable element 36 may be inflated and have a variety of different diameters. Where there is more than one expandable element 36, each expandable element 36 may have the same diameter or each expandable element 36 may have different diameters. Additionally, where there is more than one expandable element 36, each individual expandable may have different diameters within the same expandable element 36. The different diameters may be sized to accommodate different anatomical structures and may be customized for a patient.

The expandable element 36 may be on only a portion of the distal portion 32 of the elongate body 28 or the expandable element 36 may surround the distal portion 32 of the elongate body 28. The size and shape of the expandable element 36 may depend upon how and where the medical device 10 is being used and which part of the body/anatomical structure the expandable element 36 is going to come into contact with. Having the expandable element 36 in fluid communication with the lumen 34 enables the inflation and deflation of the expandable element 36 using the at least one port 22 and an inflation and deflation device.

The expandable element 36 may be expandable by inflation which may be done using a pressurized fluid and/or air that is able to inflate the expandable element 36. For example, the expandable element 36 may be at least one inflatable balloon which can be used to dilate or expand a portion of a patient's body such as a vessel, a part of the heart, or another part of the body/anatomical structure. Alternatively, the expandable element 36 may include other expandable structures including tubes which can expand, self-expandable structures comprising shape-memory materials, or superelastic materials. The expandable element 36 may be, for example, at least one balloon constructed from polyethylene terephthalate, nylon, polyurethane, and/or latex. The expandable element 36 may have a length from the first end 38 to the second end 40 of approximately 4 centimeters and the at least one diameter 37 may be approximately 8.5 millimeters. In other embodiments, the expandable element 36 may have different dimensions.

A cannula 42 may surround a portion of the elongate body 28. The cannula 42 may be coupled with the elongate body 28 and may further include a coupling mechanism used to couple the cannula 42 with the elongate body 28. The cannula 42 and the elongate body 28 may be permanent coupled, releasably coupled, and/or slidably coupled together. In one embodiment, the cannula 42 may be coaxial with the elongate body 28. The cannula 42 may be freely or restrictably slidable with respect to the elongate body 28 along the longitudinal axis 35 of the elongate body 28. The cannula 42 may have a proximal end 44 and a distal end 46 and the distal end 46 of the cannula 42 may be disposed proximal and adjacent to the second end 40 of the expandable element 36. The proximal end 44 of the cannula 42 may include a valve 45. The valve 45 may be temporary or permanent and may help to prevent blood loss when the medical device 10 is in use. The valve 45 may be a one-way or two-way valve and may be disposed anywhere on the cannula 42. Alternatively, more than one valve 45 may be used with the medical device 10. The distal end 46 of the cannula 42 may be substantially co-terminus with the second end 40 of the expandable element 36. In an alternative embodiment, the cannula 42 may be disposed proximal and adjacent to the first end 38 of the expandable element 36 or in another location.

The outer diameter 48 of the cannula 42 may be substantially equal to or lesser than an outer diameter 50 of the expandable element 36 when the expandable element 36 is inflated. Alternatively, the outer diameter 48 of the cannula 42 may be greater than the outer diameter 50 of the expandable element 36 when it is inflated. As a non-limiting example, the outer diameter 48 of the cannula 42 and the outer diameter 50 of the expandable element 36 may be at least 8.5 millimeters and/or less than 8.5 millimeters. The outer diameter 48 of the cannula 42 and the outer diameter 50 of the expandable element 36 may be the same diameter or each may have different diameters and may be dependent upon how much the expandable element 36 is inflated.

The distal portion 18 may further include a tip 52 and the tip 52 may have an aperture 54 or in an alternative embodiment it may not have any aperture 54. In one embodiment, the tip 52 may include at least one electrode which could heat or cool the tissue that it comes into contact with. The tip 52 may be disposed on the distal portion 32 of the elongate body 28 or it may be disposed in a different location on the elongate body 28. Additionally, the tip 52 may have one aperture 54 or it may have more than one aperture 54 where each of the apertures 54 are the same size or different sizes. The aperture 54 may be in fluid communication with the lumen 34 such that a medical device may be placed inside the lumen 34 and through the aperture 54 such that the medical device that moves through the aperture 54 may come into contact with tissue. The tip 52 may include a proximal portion 56, a distal portion 58, and a longitudinal axis 60 extending from the proximal portion 56 to the distal portion 58 of the tip 52. The tip 52 may taper in diameter from the proximal portion 56 to the distal portion 58 along the longitudinal axis 60. The tip 52 may also increase in diameter from the proximal portion 56 to the distal portion 58 along the longitudinal axis 60 or the tip 52 may have the same diameter from the proximal portion 56 to the distal portion 58 along the longitudinal axis 60.

As a non-limiting example, a medical device such as a puncturing device 24, may be inserted into the lumen 34 and the aperture 54 may be sized to receive the puncturing device 24 so that the puncturing device 24 may come into contact with tissue that is in close proximity to the aperture 54. The puncturing device 24 may include, but not be limited to a needle, the guidewire 26, or any other device that can be used to puncture tissue. The puncturing device 24 may be used to create an orifice 62 and when the orifice 62 is created by the puncturing device 24, the tip 52 may be inserted into the orifice 62 and as the tip 52 progresses through the orifice 62, the orifice 62 may enlarge depending upon the dimensions of the tip 52. Alternatively, the tip 52 may not have a width that tapers and may be the same width throughout or the width of the tip 52 may taper in diameter from the distal portion 58 to the proximal portion 56 along the longitudinal axis 60. The width of the tip 52 and how the tip 52 is configured may depend upon the size of the cannula 42 that may be fixated in the orifice 62 and the size orifice 62 that is desired. The orientation of the tip 52 may determine how the orifice 62 is sized and created. The size and shape of the tip 52 may be customized based upon the anatomical structures that it is going to come into contact with.

Figure 3:
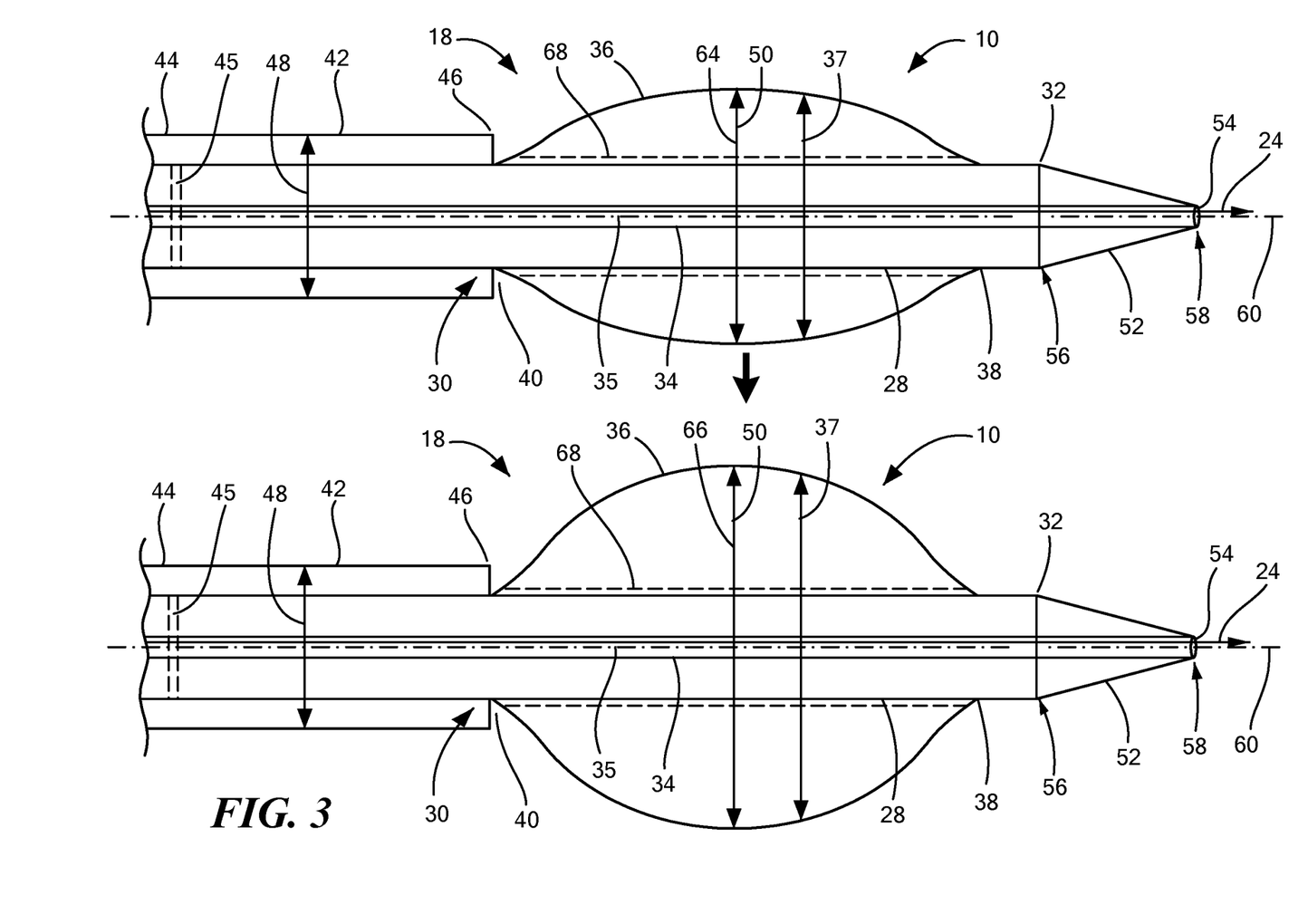
FIG. 3 is a perspective view of the distal portion from the medical device in FIG. 1 with an expandable element deflated and inflated.

As shown in FIG. 3, the expandable element 36 that is inflatable to at least one diameter 37 may be inflatable a first diameter 64 and a second diameter 66. In an alternative configuration, the expandable element 36 may be inflatable to a variety of different diameters depending upon the size of the orifice 62 that is being created. In FIG. 3, the expandable element 36 moves from a deflated configuration to an inflated configuration. If only a small orifice 62 is going to be created, the expandable element 36 may be inflated to a first diameter 64 and if a larger orifice 62 is desired, then the expandable element 36 may be inflated to a second diameter 66. The at least one expandable element may include a longitudinal axis 68 extending from the first end 38 to the second end 40 and the length of the expandable element 36 along the longitudinal axis 68 may be between 1 cm and 6 cm. Alternatively, the length of the expandable element 36 may be less than 1 cm or it may also be more than 6 cm. In an alternative embodiment, there may be more than one expandable element 36 and each expandable element 36 may be the same length or each may have a different length.

Figure 4:
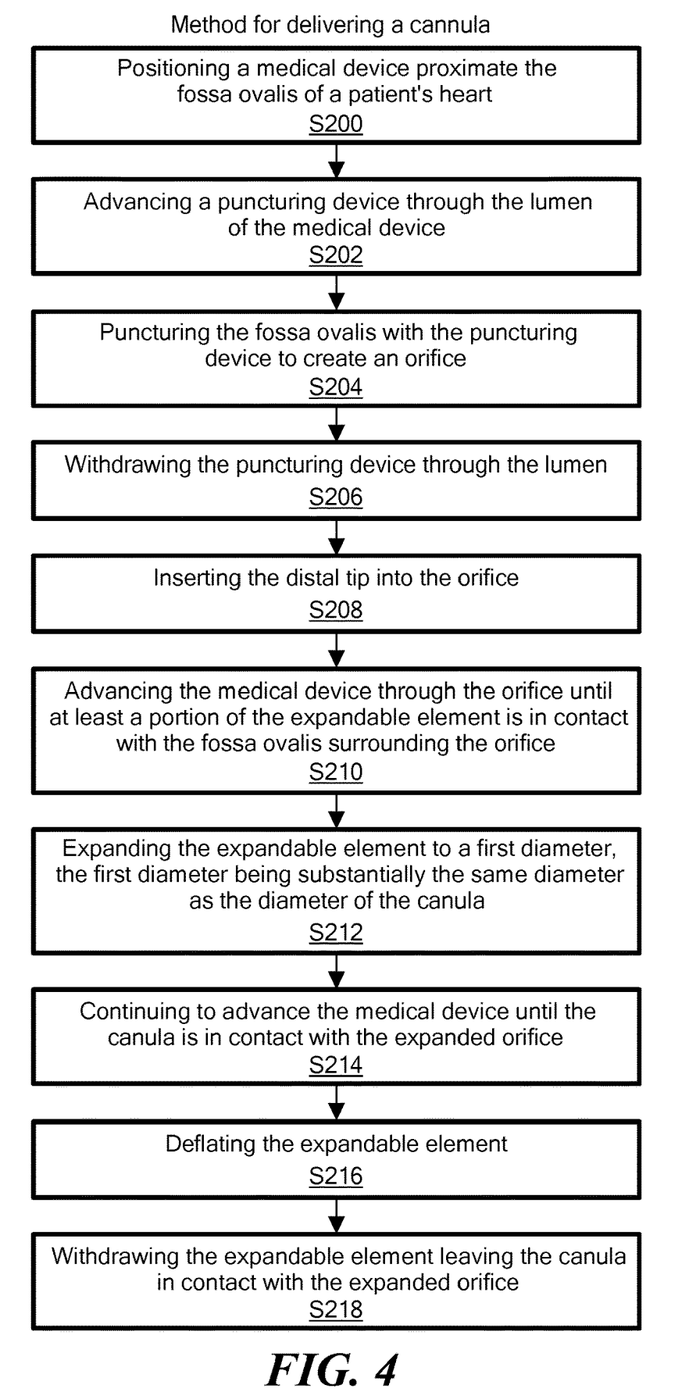
FIG. 4 is a method for using the medical device.

As shown in FIG. 4, the medical device 10 may be positioned in the fossa ovalis of a patient's heart. The medical device 10 may be positioned proximate the fossa ovalis of a patient's heart. S200. The puncturing device 24 may be advanced through the lumen 34 of the medical device 10. S202. The puncturing device 24 may be used to puncture the fossa ovalis to create an orifice 62. S204. Once the puncturing device 24 has created the orifice 62, the puncturing device 24 may be withdrawn through the lumen 34. S206. The distal portion 58 of the tip 52 may be inserted into the orifice 62. S208. The medical device 10 may be advanced through the orifice 62 until at least a portion of the expandable element 36 is in contact with the fossa ovalis surrounding the orifice 62. S210. Once the expandable element 36 is in contact with the fossa ovalis surrounding the orifice 62, the expandable element 36 may be expanded to a first diameter 64 and the first diameter 64 may be substantially the same diameter as the outer diameter 48 of the cannula 42 or it may be a greater diameter or a lesser diameter than the outer diameter 48 of the cannula 42. S2012. The medical device 10 may continue to be advanced until the cannula 42 is in contact with the expanded orifice 62. S214. The expandable element 36 may be deflated. S216. The expandable element 36 may be withdrawn from the orifice 62 such that the cannula 42 remains in contact with the expanded orifice 62. S218. These steps are shown in more detail below in FIG. 5 with how the medical device is moved and positioned within the fossa ovalis of a patient's heart.

Figure 5:
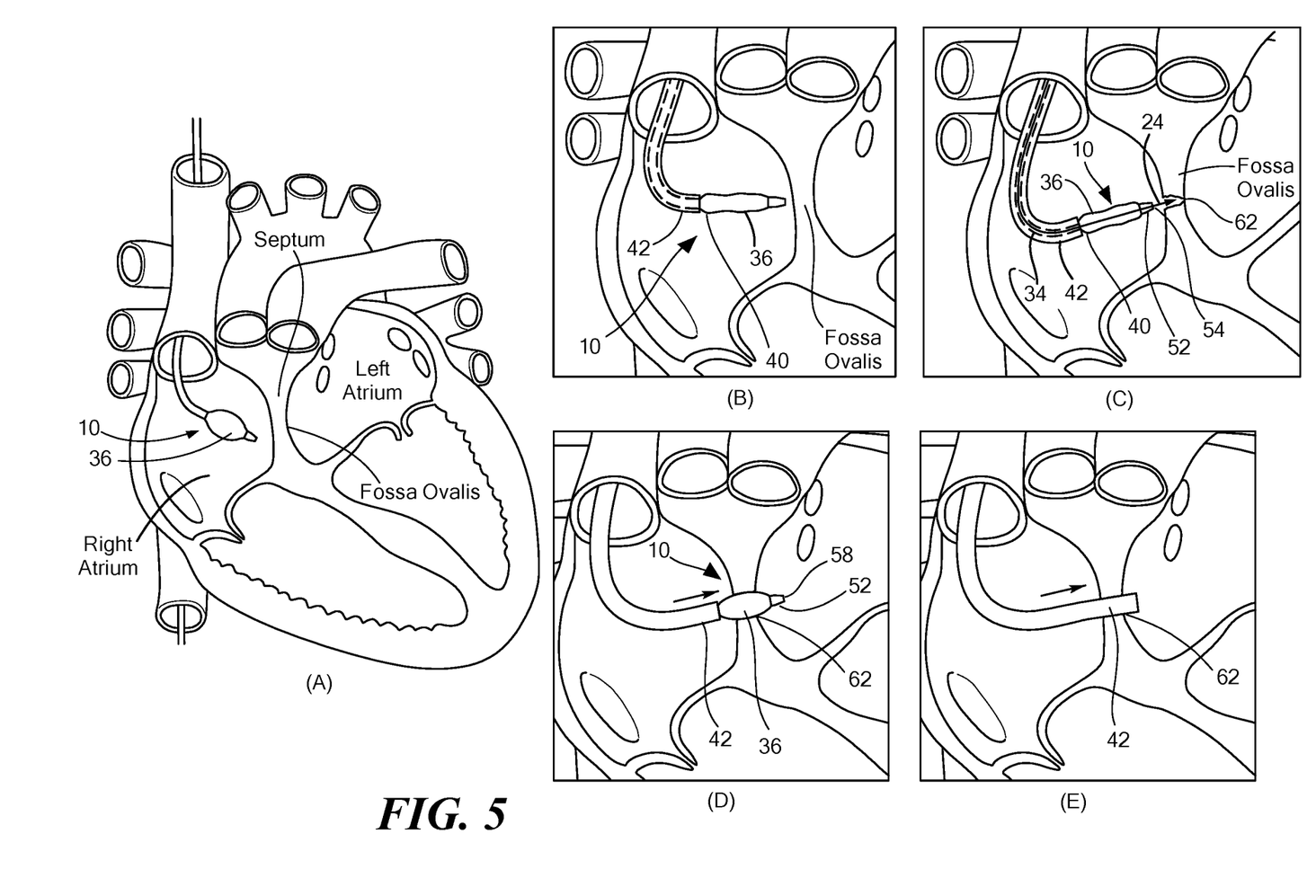
FIG. 5 is a view of the medical device shown in FIG. 1 being inserted into the septum of the heart.

In FIG. 5, the medical device 10 is shown as positioned in the fossa ovalis of a patient's heart (FIGS. 5D and 5E). Before the medical device 10 is introduced into a patient's vasculature, the expandable element 36 may be inflated and then inserted into the vasculature to create a smooth transition into the vasculature and through the vasculature using the inflated expandable element 36 (FIG. 5A). The diameter of the expandable element 36 may remain consistent or it may be changed as the medical device 10 moves throughout the body to accommodate different anatomical structures. The medical device 10 and the catheter body 12 may be flexible to allow for easy movement though the vasculature. Additionally, the catheter body 12 may include the actuator 27 with the deflection component or other component to allow the medical device 10 to curve and move through the vasculature. The medical device 10 may be moved through the patient's vasculature, which may include the superior vena cava, the inferior vena cava, or any other portion of the vasculature, and positioned in the right atrium of the heart (FIGS. 5A-5E). Once the medical device 10 reaches the right atrium, the expandable element 36 may be deflated (FIG. 5B). Alternatively, the expandable element 36 may remain in an inflated state as well.

After the expandable element 36 is deflated, the cannula 42 may be positioned proximate the second end 40 of the expandable element 36. The medical device 10 may then be disposed proximate the fossa ovalis of a patient's heart and the puncturing device 24 may be introduced into the lumen 34 and advanced through the lumen 34 of the medical device 10 (FIG. 5C). The puncturing device 24 may travel through the lumen and exit from the aperture 54 of the tip 52 so that the puncturing device 24 may be used to puncture the fossa ovalis to create the orifice 62. Once the puncturing device 24 has created the orifice 62, the puncturing device 24 may be withdrawn through the lumen 34. The distal portion 58 of the tip 52 may be inserted into the orifice 62 and the medical device 10 may be advanced through the orifice 62 until at least a portion of the expandable element 36 is in contact with the fossa ovalis surrounding the orifice 62 (FIG. 5D). Additionally, at least a portion of the medical device 10 may be in the left atrium of the patient's heart (FIGS. 5D and 5E). Once at least a portion of the expandable element 36 is in contact with the fossa ovalis surrounding the orifice 62, the expandable element 36 may be expanded to a first diameter 64 (FIG. 5D). The first diameter 64 may be the same diameter as the outer diameter 48 of the cannula 42 or it may be a greater diameter or a lesser diameter than the outer diameter 48 of the cannula 42. The medical device 10 may be advanced further until the cannula 42 is in contact with the expanded orifice 62 to a desired size (FIG. 5E). The cannula 42 may provide the medical device 10 with support so that the cannula 42 may be advanced through the orifice 62. While the expandable element 36 has expanded the orifice 62 to a particular size, the cannula 42 may be moved into the orifice 62 in the septum (FIG. 5E). The expandable element 36 may be deflated and then withdrawn from the orifice 62 such that the cannula 42 remains in contact with the expanded orifice 62. The cannula 42 may be fixated in a desired position in the orifice 62 of the septum (FIG. 5E). The medical device 10 may also be used in any portion of a patient's vasculature and is not limited to the heart. How the medical device 10 is inserted and maneuvered throughout the body will depend upon the anatomical structure of the patient as well as the portion of the body that the medical device is being maneuvered within.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device comprising:
    an elongate body having a proximal portion, a distal portion, and defining a lumen therethrough, the distal portion comprising a tip configured to be inserted through an orifice in a tissue of a patient;
    an expandable element coupled to the distal portion of the elongate body and in fluid communication with the lumen, the expandable element defining a first end and a second end, wherein the first end of the expandable element is distal to the second end of the expandable element; and
    a cannula surrounding at least a portion of the elongate body, an outer diameter of the cannula being substantially equal to or lesser than an outer diameter of the expandable element when inflated,
    wherein the orifice through which the tip is inserted has a diameter less than the outer diameter of the cannula, and wherein the expandable element is configured to be inflated within the orifice to dilate the orifice to enable the cannula to be inserted into the orifice, and
    wherein a distal end of the cannula is configured to be substantially co-terminus with the second end of the expandable element as the elongate body progresses through the orifice.

2. The medical device of claim 1, wherein the expandable element is a balloon.

3. The medical device of claim 2, wherein the balloon is constructed from at least one of polyethylene terephthalate, nylon, polyurethane, or latex.

4. The medical device of claim 1, wherein the cannula is coaxial with the elongate body.

5. The medical device of claim 1, wherein the tip comprises an aperture in fluid communication with the lumen.

6. The medical device of claim 1, wherein the tip has a proximal portion, a distal portion, and a longitudinal axis extending therethrough, the tip tapering in diameter from the proximal portion of the tip to the distal portion of the tip along the longitudinal axis, and wherein the tip is configured to enlarge the orifice as the tip progresses through the orifice to define an enlarged orifice, and wherein the expandable element is configured to be inflated within the enlarged orifice to dilate the enlarged orifice to enable the cannula to be inserted into the orifice.

7. The medical device of claim 1, wherein the outer diameter of the cannula and the outer diameter of the expandable element are at least 8.5 millimeters.

8. The medical device of claim 1, wherein the outer diameter of the cannula and the outer diameter of the expandable element are less than 8.5 millimeters.

9. The medical device of claim 1, wherein the cannula and the elongate body are coupled together.

10. The medical device of claim 9, wherein the elongate body is constructed from a block copolymer.

11. The medical device of claim 1, wherein the elongate body further includes a longitudinal axis extending from the proximal portion to the distal portion, the cannula being slidable with respect to the elongate body along the longitudinal axis.

12. The medical device of claim 1, wherein the cannula comprises a valve configured to control a flow of a fluid in the cannula, an entirety of the valve being disposed within the cannula.

13. The medical device of claim 1, wherein the outer diameter of the cannula is substantially equal to the outer diameter of the expandable element when the expandable element is inflated.

14. A medical device comprising:
an elongate body having a proximal portion and a distal portion, the elongate body defining a lumen therethrough;
at least one expandable element surrounding the distal portion of the elongate body, the at least one expandable element being configured to expand to a first diameter, wherein the at least one expandable element defines a first end and a second end, the first end being opposite the second end, wherein the first end of the at least one expandable element is distal to the second end of the at least one expandable element; and
a cannula having a proximal portion and a distal portion opposite the proximal portion of the cannula, the cannula being disposed around the elongate body the cannula having a second diameter that is substantially the same as the first diameter,
the distal portion of the elongate body further including a tip with a proximal portion, a distal portion, a longitudinal axis extending therethrough, and an aperture which is in fluid communication with the lumen, the tip tapering in diameter from the proximal portion of the tip to the distal portion of the tip along the longitudinal axis and being configured to enlarge an orifice created by a puncturing device, wherein the tip is configured to enlarge the orifice in a tissue of a patient as the tip progresses through the orifice to define an enlarged orifice, and wherein the at least one expandable element is configured to be inflated within the enlarged orifice to dilate the enlarged orifice,
wherein a distal end of the cannula is configured to be substantially co-terminus with the second end of the at least one expandable element as the elongate body progresses through the orifice.

15. The medical device of claim 14, wherein the at least one expandable element is at least one balloon.

16. The medical device of claim 14, wherein the first diameter and the second diameter are at least 8.5 millimeters.

17. The medical device of claim 14, wherein the at least one expandable element further includes a longitudinal axis extending from the first end to the second end and a length of the at least one expandable element along the longitudinal axis of the at least one expandable element is between 1 cm and 6 cm.

18. The medical device of claim 14, wherein the proximal portion of the cannula comprises a valve configured to control a flow of a fluid in the cannula, an entirety of the valve being disposed within the cannula.

19. A method for delivering a cannula, comprising:
positioning a medical device proximate a fossa ovalis of a patient's heart, the medical device including:
an elongate body having a proximal portion, a distal portion, and defining a lumen therethrough;
an expandable element coupled to the distal portion of the elongate body and in fluid communication with the lumen, the expandable element defining a first end and a second end, the second end being proximal to the first end, wherein the first end of the expandable element is distal to the second end of the expandable element;
the cannula surrounding at least a portion of the elongate body, the cannula defining a proximal end and a distal end, the distal end of the cannula being disposed proximal and adjacent to the second end of the expandable element, the cannula having an outer diameter; and
the distal portion of the elongate body further including a tip;
advancing a puncturing device through the lumen of the elongate body of the medical device;
puncturing the fossa ovalis with the puncturing device to create an orifice, wherein the orifice has a diameter less than the outer diameter of the cannula;
withdrawing the puncturing device through the lumen;
inserting the tip through the orifice;
advancing the medical device through the orifice until at least a portion of the expandable element is in contact with the fossa ovalis surrounding the orifice, wherein the distal end of the cannula is configured to be substantially co-terminus with the second end of the expandable element as the elongate body advances through the orifice;
expanding the expandable element to a first diameter within the orifice to dilate the orifice and enable the cannula to be inserted through the orifice, the first diameter being substantially a same diameter as the outer diameter of the cannula;
continuing to advance the medical device until the cannula is in contact with the orifice and extending through the orifice;
deflating the expandable element; and withdrawing the expandable element leaving the cannula in contact with and extending through the orifice.

* * * * *